US010029978B2

(12) United States Patent
Bernard

(10) Patent No.: US 10,029,978 B2
(45) Date of Patent: Jul. 24, 2018

(54) CYCLOALIPHATIC AND ALIPHATIC DIAMINE-BASED FATTY ACID DIAMIDES USED AS ORGANOGELATORS

(71) Applicant: Arkema France, Colombes (FR)

(72) Inventor: Michael Y. Bernard, Enghien les Bains (FR)

(73) Assignee: Arkema France, Colombes (FR)

( * ) Notice: Subject to any disclaimer, the term of this patent is extended or adjusted under 35 U.S.C. 154(b) by 130 days.

(21) Appl. No.: 14/906,312

(22) PCT Filed: Jul. 18, 2014

(86) PCT No.: PCT/FR2014/051844
§ 371 (c)(1),
(2) Date: Jan. 20, 2016

(87) PCT Pub. No.: WO2015/011375
PCT Pub. Date: Jan. 29, 2015

(65) Prior Publication Data
US 2016/0168079 A1 Jun. 16, 2016

(30) Foreign Application Priority Data

Jul. 25, 2013 (FR) ..................................... 13 57347

(51) Int. Cl.
*C07C 235/16* (2006.01)
*C07C 235/10* (2006.01)
*C09D 5/04* (2006.01)
*C09D 163/00* (2006.01)
*C09D 5/34* (2006.01)
*C09D 7/63* (2018.01)
*C08K 5/20* (2006.01)
*C09D 7/00* (2018.01)

(52) U.S. Cl.
CPC .......... *C07C 235/16* (2013.01); *C07C 235/10* (2013.01); *C09D 5/04* (2013.01); *C09D 5/34* (2013.01); *C09D 7/63* (2018.01); *C09D 163/00* (2013.01); *C07C 2601/14* (2017.05); *C08K 5/20* (2013.01); *C09D 7/00* (2013.01)

(58) Field of Classification Search
CPC . C07C 235/16; C07C 235/10; C07C 2601/14; C09D 5/04; C09D 5/34; C09D 7/001; C09D 7/1233; C09D 163/00; C09D 7/00; C08K 5/20; Y10T 428/2983
USPC ........................................................ 428/402
See application file for complete search history.

(56) References Cited

U.S. PATENT DOCUMENTS

| 3,977,894 | A | * | 8/1976 | White | C01B 33/44 106/272 |
|---|---|---|---|---|---|
| 2009/0203852 | A1 | * | 8/2009 | Urakami | C08L 67/04 525/418 |
| 2009/0223409 | A1 | * | 9/2009 | Banning | C07C 233/05 106/31.13 |
| 2011/0060081 | A1 | * | 3/2011 | Banning | C07C 233/05 524/226 |
| 2011/0061565 | A1 | * | 3/2011 | Banning | C07C 233/05 106/31.13 |
| 2011/0061566 | A1 | * | 3/2011 | Banning | C07C 233/05 106/31.13 |
| 2011/0065850 | A1 | * | 3/2011 | Banning | C07C 233/05 524/226 |
| 2011/0100254 | A1 | * | 5/2011 | Banning | C07C 233/05 106/31.75 |
| 2012/0227622 | A1 | * | 9/2012 | Banning | C07C 233/05 106/31.29 |

FOREIGN PATENT DOCUMENTS

| EP | 2045293 | * | 4/2009 |
| EP | 2098502 | * | 9/2009 |
| JP | 3-168647 | * | 7/1991 |
| JP | 10-328882 | * | 12/1998 |
| WO | WO2014/016517 | * | 1/2014 |
| WO | WO 2014/016517 A1 | | 1/2014 |

* cited by examiner

*Primary Examiner* — Leszek Kiliman
(74) *Attorney, Agent, or Firm* — Lynn B. Morreale

(57) ABSTRACT

The invention relates to a fatty diamide comprising or consisting of a reaction product obtained from:
a) at least one cycloaliphatic diamine comprising a ring of 6 carbon atoms,
b) a fatty hydroxy acid chosen from 12-hydroxystearic acid (12-HSA), 9-hydroxystearic acid (9-HSA), 10-hydroxystearic acid (10-HSA), 14-hydroxyeicosanoic acid (14-HEA) or binary or ternary or quaternary mixtures thereof,
c) at least a second diamine chosen from linear aliphatic $C_2$ to $C_{12}$ primary diamines,
d) optionally, at least one monoacid chosen from saturated and non-hydroxylated linear $C_6$ to $C_{16}$ carboxylic acids,
e) optionally, at least a third primary diamine different from c) chosen from linear aliphatic $C_2$ to $C_{12}$ diamines.
f) at least one aromatic amine chosen from xylylenediamines, said aromatic diamine possibly being partially or totally replaced with said diamine a).
The invention also covers the use of this diamide as an organogelling agent, in particular as a rheology additive, for coating, glue, adhesive or cosmetic, stripping, molding, mastic or sealing compositions.

18 Claims, No Drawings

CYCLOALIPHATIC AND ALIPHATIC DIAMINE-BASED FATTY ACID DIAMIDES USED AS ORGANOGELATORS

CROSS-REFERENCE TO RELATED APPLICATIONS

This application is a national stage application under 35 U.S.C. § 371 of PCT/FR2014/051844, filed Jul. 18, 2014, which claims benefit to French patent application FR 13.57347, filed Jul. 25, 2013.

The invention relates first to a fatty acid diamide comprising in its structure both cycloaliphatic and aliphatic diamines with a specific mole ratio, and to the use of this product as an organogelling agent or as rheology agent or additive, in particular in coating, moulding, mastic or sealing, stripping or cosmetic compositions.

U.S. Pat. No. 3,977,894 describes self-activatable rheology additives based on a homogeneous mixture of organoclays, glyceryl tris(12-hydroxystearate) and a fatty amide based on a $C_2$ to $C_{18}$ aliphatic diamine and 12-hydroxystearic acid.

Rheology additives, in particular thixotropic agents based on diamides comprising, as diamine component, an aliphatic amine and xylylenediamine, and in particular m-xylylenediamine, are already known with advantageous performance qualities. However, given the environmental constraints associated with its toxicity and above all its potential effects on health during its handling, the question of its at least partial replacement to reduced levels and preferably its total replacement has arisen. Such a replacement should not, however, significantly affect the rheology performance qualities of the fatty diamides obtained. More particularly, the target diamides should have high performance qualities, in terms of thixotropic effect and of sag resistance, with activation conditions imposed at relatively low temperature, i.e. from 40° C. to less than 80° C. This corresponds in particular to the case of binder compositions in a reactive or non-reactive organic solvent medium, which solvent should not via an evaporation effect or via a reaction effect be subjected to high activation temperatures and should not pose a risk to the environment and health if there is emission of solvent vapours at high temperature nor a risk to the stability of the binder composition if said solvent is liable to react by heating to higher temperature. In addition, no significant impairment of the final application performance qualities should occur. This problem is above all valid for coating compositions such as paints, varnishes, inks and gel coats, as they are currently known, or glues or adhesives or stripping or moulding or cosmetic agents in a reactive or non-reactive organic solvent medium. For example, a non-reactive-type solvent used in paints is xylene. Examples of reactive solvents (also known as reactive diluents) that may be mentioned are styrene or acrylic monomers in gel coat or moulding compositions based on unsaturated polyesters or vinyl esters.

The affinity of m-xylylenediamine and of diamides based on this diamine and 12-hydroxystearic acid relative to the solvents used in the application compositions, in particular in coatings or glues or adhesives, makes this diamine an essential component for organogelling additives or rheology additives, suitable for these applications. More particularly, in coatings such as paints, varnishes and inks in a non-reactive solvent medium, such as xylene, the question of its replacement demands the search for a good compromise of performance qualities in this solvent and with the organic binders that may be used in this medium, and without significantly affecting the rheology performance qualities during the final application.

Depending on the parameters associated with the working medium, parameters associated with the specific composition (molecular and structural parameters) and other parameters associated with the activation conditions in a given system, the rheological performance qualities may vary significantly and it is very difficult to extrapolate and to predict these performance qualities in general from what is known for performance qualities of a very particular known system. The effect of gelation in a particular target application medium necessitates a specific compromise between the capacity of the amide to be solubilized (with a specifically limited target solubility) and associated with the capacity to form crystalline fibres and the tendency towards precipitation and sedimentation in said medium based on said organic solvent. The term "solvent" in the definitions given above and below should be understood as a main organic solvent that cannot be subjected to (is not capable of) activation at high temperature, in particular above 90° C. Consequently, said solvent according to the invention is capable of being activated only at temperatures below 90° C.

Thus, the aim of the present invention is to overcome the outlined drawbacks and is therefore directed towards developing novel fatty diamides of specific and selective composition. This composition comprises diamines of cycloaliphatic structure in partial replacement and more particularly in total replacement for xylylenediamines, in particular for m-xylylenediamine in the presence of at least one aliphatic diamine as essential amine components of said diamides in specific ratios. The invention is thus directed towards organogelling agent performance qualities that are satisfactory and in particular at least as good as those of organogelling agents based on xylylenediamine alone (100% of the amine component), i.e. without any replacement with said cyclic diamine, taken as comparison reference. The diamides according to the invention are particularly capable of being activated at low temperature as described above.

The advantages of the present invention, relative to the products and uses of the prior art in the field of binder compositions in organic solvent medium, are rheological performance qualities that are satisfactory and preferably at least as good as those obtained with amides based on m-xylylenediamine alone (in the total absence of cycloaliphatic diamine) with at least equivalent performance qualities. These performance qualities are obtained without having the environmental and health constraints associated with the toxicity of said aromatic diamine.

The present invention first covers said diamide of specific composition.

The second subject of the invention concerns the use of said diamide as an organogelling agent.

Another subject is the organogelling agent comprising said diamide.

Finally, the invention relates to a binder composition comprising said diamide for various uses.

Thus, the first subject of the invention relates to a characterized fatty acid diamide which comprises at least one reaction product obtained from a reaction mixture comprising:

a) at least one cycloaliphatic diamine comprising a ring of 6 carbon atoms and in particular globally comprising, including said ring, from 6 to 18 carbon atoms, said diamine preferably being chosen from: 1,3-bis(aminomethyl)cyclohexane (1,3-BAC), 1,4-bis(aminomethyl)cyclohexane (1,4-BAC), 1,2-bis-(aminomethyl)cyclohexane (1,2-BAC) and isomer mixtures thereof, decahydronaphthalenediamines, isophoronediamines, more preferentially 1,3-bis-(aminomethyl)cyclohexane (1,3-BAC), 1,4-bis(aminomethyl)cyclohexane (1,4-BAC), and even more preferentially 1,3-bis(aminomethyl)cyclohexane (1,3-BAC), b) a fatty hydroxy acid chosen from 12-hydroxystearic acid (12-HSA), 9-hydroxystearic acid (9-HSA), 10-hydroxystearic acid (10-HSA), 14-hydroxyeicosanoic acid (14-HEA) or binary or ternary or quaternary mixtures thereof, preferably 12-hydroxystearic acid or a binary or ternary mixture of 12-hydroxystearic acid with the other hydroxy acids mentioned, c) at least a second diamine selected from linear primary aliphatic $C_2$ to $C_{12}$, preferably $C_2$ to $C_8$ and more preferentially $C_2$ to $C_6$ diamines, d) optionally, at least one monoacid selected from saturated and non-hydroxylated linear $C_6$ to $C_{18}$ preferably $C_6$ to $C_{15}$ and more preferentially $C_6$ to $C_{12}$ carboxylic acids, e) optionally, at least a third primary diamine different from c) selected from linear aliphatic $C_2$ to $C_{12}$, preferably $C_2$ to $C_8$ and more preferentially $C_2$ to $C_6$ diamines, f) at least one aromatic diamine chosen from xylylenediamines, preferably from m-, p-xylylenediamines (m-, p-XDA), more preferentially m-xylylenediamine (m-XDA), said aromatic diamine possibly being partially or totally replaced with a cycloaliphatic diamine as defined in point a).

According to a preferred option, the molar percentage of a/(a+f) is at least 50% and ranges up to 100% and the molar percentage of (a+f)/(a+c+e+f) which represents the mole ratio of the cycloaliphatic amine a) and aromatic amine f) relative to all of the amines, ranges from 30% to 80% and preferably from 30% to 65%. More particularly, the mole ratio a/(c+e) of the diamine a) to the other aliphatic diamines is at least 0.25 and preferably ranges from 0.45 to 0.95 and more preferentially from 0.5 to 0.85.

The term "linear" has a meaning, relative to a branched structure, only for chains comprising at least 4 carbon atoms and means for these chains the absence of any branching, chains of shorter length ($C_2$ and $C_3$) being by definition always linear.

According to another possibility of the present invention, said cycloaliphatic diamine a), preferably 1,3-BAC or 1,4-BAC, is in the presence of xylylenediamines f), preferably p-XDA or m-XDA, more preferentially m-XDA, with said diamine a) representing from 50 mol % to 99 mol % of the total number of moles of diamine a)+xylylenediamines f), preferably from 60% to 99% of said total number.

According to an alternative and more preferred option of the invention, said diamine f) is absent (0%) with a mole ratio a/(a+f) of 100%, preferably with said cycloaliphatic diamine a) being 1,4-BAC or 1,3-BAC. Said diamine a) may be present alone or in the form of a mixture comprising said diamine a).

According to a more particular option, said diamide according to the invention comprises:

i) a diamide consisting of the product of reaction of 1 mol of said diamine a) with 2 mol of said hydroxy acid b) as defined above, preferably said hydroxy acid b) being the 12-hydroxystearic acid, and ii) a diamide consisting of the product of reaction of 1 mol of diamine c) with 2 mol of said hydroxy acid b) as defined above, preferably said hydroxy acid b) being the 12-hydroxystearic acid, and iii) a diamide consisting of the product of reaction of 1 mol of diamine according to e) and of 2 mol of said hydroxy acid b) as defined above, preferably said hydroxy acid b) being the 12-hydroxystearic acid.

The diamide of the invention may comprise at least 2 and preferably at least 3 different reaction products as derived from the reaction between said diamines a), c) and e) and optionally xylylenediamines f) and monoacids b) and optionally d).

According to a particular mode, said monoacid d) is present in a proportion such that the mole ratio d/(b+d) is less than 0.5 and preferably ranges between 0.02 and 0.5.

According to a particular preference, said diamide of the invention is in the form of a micronized powder, preferably in the form of a powder with a mean size by volume of less than 20μ and more preferentially less than 15μ. The determination of said size may be performed with measuring apparatus equipped with a laser detector.

The micronization is performed by mechanical milling optionally followed by screening or by air jet milling to obtain the finest powders with a controlled and narrower particle size distribution.

The second subject of the invention concerns the use of the diamide of the invention as an organogelling agent in organic solvent medium.

Thus, said additive may be used as a rheology additive, in particular in the form of a preactivated paste preconcentrated in an organic solvent. The organic solvent may be a mixture of solvents. Preferably, it is a polar solvent or comprises at least one polar solvent. A preferred important use of said diamide is a use (as rheology additive) in a coating composition in particular in paints, varnishes, inks and gel coats or in a glue and adhesive or stripping or moulding or cosmetic composition. More preferentially, said use concerns a coating composition, taking into account the questions posed by affinity in these media of the m-xylylenediamine to be replaced according to the object of the invention, as explained above.

Another subject of the invention is an organogelling agent, in particular rheology additive which comprises at least one diamide as defined according to the invention, as described above. More particularly, it may be a rheology agent or additive, in particular a thixotropic agent in a composition preconcentrated in at least one organic solvent, including a mixture of solvents, preferably in at least one polar organic solvent, in the form of a preactivated paste.

The term "polar organic solvent" according to the above description includes in its definition or should be interpreted as meaning "at least one polar organic solvent" or "a mixture of organic solvents comprising at least one polar organic solvent". A solvent considered as being a polar organic solvent is a solvent comprising at least one polar group, for instance an alcohol or ester group. As examples of polar organic solvents according to the first interpretation option, mention may be made of an alcohol such as ethanol or butanol or a mixture thereof and, according to the second interpretation option (mixture of organic solvents comprising at least one polar organic solvent), a mixture of such an alcohol (ethanol or butanol) with a non-polar solvent, for instance xylene.

Finally, the invention covers an organic binder composition, which comprises, as rheology agent (or additive being a term equivalent to agent), at least one diamide as defined above according to the invention.

More particularly, this organic binder composition is a coating, paint, varnish, ink or gel coat composition or a glue or adhesive composition or stripping or moulding or cosmetic composition. According to a more preferred option, said composition is a coating composition. According to another possibility, said composition is a mastic or sealing composition. According to another option, this composition is a moulding composition. Moulding or gel coat or radiation-crosslinkable coating compositions are compositions in reactive solvent medium (also known as reactive diluent), such as unsaturated polyesters or vinyl esters in styrene or in another equivalent comonomer or multifunctional acrylic (meaning acryl) monomers and/or oligomers, said oligomers using as reactive diluent a multifunctional acrylic monomer.

More specifically, said organic binder may be selected from: epoxy resins, unsaturated polyesters, vinyl esters, alkyds, silane resins, polyurethanes, polyester amides, solvent-based (non-reactive diluent) acrylic resins, acrylic (multifunctional) monomers and/or oligomers with, in the latter case, the reactive diluent being an acrylic (multifunctional) monomer or chlorinated elastomers and non-chlorinated elastomers and chlorinated polymers other than chlorinated elastomers, preferably epoxy resins, unsaturated polyesters, vinyl esters, alkyds, polyurethanes, polyester amides, solvent-based acrylic resins and said acrylic monomers and/or oligomers or chlorinated elastomers and non-chlorinated elastomers.

Acrylic monomers and/or oligomers mean monomers and/or oligomers bearing at least one acrylate or methacrylate function and in particular multifunctional, i.e. with at least two of said acrylate or methacrylate functions per molecule.

The examples presented below are given as illustrations of the invention and of its performance qualities and do not in any way limit its scope.

EXPERIMENTAL SECTION

I—Starting Materials Used

TABLE 1

Starting materials used

| Product | Function | Commercial reference | Supplier |
|---|---|---|---|
| Hexamethylenediamine | Component vs amide | Hexamethylenediamine 98% | Aldrich |
| meta-Xylylenediamine | Component vs amide | mXDA | Mitsubishi Chemicals |
| 1,3-Bis(aminomethyl) cyclohexane | Component vs amide | 1,3-BAC | Mitsubishi Chemicals |
| 12-Hydroxystearic acid | Component vs amide | 12-HSA | Jayant Agro |
| Ethylenediamine | Component vs amide | Ethylenediamine ≥ 99.5% (GC) | Aldrich |
| Epoxy resin | Binder vs formulation | Araldite ® GZ 7071X75 | Huntsman |
| Epoxy resin | Binder vs formulation | Araldite ® GY 783 BD | Huntsman |
| Degassing agent | Degassing agent | Byk ® A530 | Byk |
| Dispersant | Dispersant | Disperbyk ® 110 | Byk |
| Titanium dioxide | Pigment | Tiona ® 595 | Société des ocres de France |
| Iron oxide | Pigment | Bayferrox ® 915 | Lubrizol |
| Zinc phosphate | Pigment | ZP 10 | Heucophos |
| Talc | Additive vs formulation | Finntalc ® MO5 | Mondo minerals |
| Silica | Filler | HPF6 | Sibelco |
| n-Butanol | Solvent | n-Butanol | Aldrich |
| Polyamide | Hardener vs binder | Crayamid ® 140 | Arkema |
| Xylene | Solvent | Xylene, reagent grade | Aldrich |

II—Methods and Tests Used

The formulations are evaluated with two tests: the flow (sag) resistance test and an evaluation of the viscosity at various speeds.

Flow Resistance Test

This is performed using a sag controller (Levelling/Sagging Tester from Sheen Instruments) which makes it possible to establish the resistance of a coating to sagging due to gravity. This controller, made of stainless steel and fitted with a flat blade, comprises notches of increasing value.

The test consists in depositing various strips of paint of parallel thickness onto a contrast card by means of the sag controller. The contrast card is immediately placed vertically, with the thinnest film at the top. The thickness at which the strips merge indicates the tendency towards sagging.

Viscosity Evaluation

This is performed using a Brookfield® RV viscometer at 25° C. (spindle: S 4). The spindle speed is set at 50 rpm (rotations per minute) and the viscosity of each paint after it has stabilized is measured. The operation is repeated for speeds of 20 rpm, 10 rpm, 5 rpm and 1 rpm.

III—Preparation and Characterization of the Diamides (or Organogelling Agents, Rheology Additives)

Example 1: Amide Based on Meta-Xylylenediamine and Hexamethylenediamine and 12-HSA 61.29 g of meta-xylylenediamine (0.46 mol), 63.8 g of ethylenediamine (i.e. 0.54 mol) and 315.2 g of 12-hydroxystearic acid (1.00 mol) are placed in a 1 liter roundbottomed flask equipped with a thermometer, Dean-Stark apparatus, a condenser and a stirrer, under a stream of nitrogen.

The mixture is heated to 200° C., still under a stream of nitrogen. The water removed begins to accumulate in the Dean Stark apparatus from 150° C. The reaction is monitored by the acid number and the amine number. When the acid and amine values are less than 10 (in mg KOH/g), the reaction mixture is cooled to 150° C. and then emptied into a silicone mould. Once it has cooled to room temperature, the product is micronized mechanically by milling and screened to obtain a fine and controlled particle size with a mean size obtained of 7 µm.

For EXAMPLES 2, 3 and 4: the same procedure was used, but with the proportions of reaction components presented in Table 2 below:

TABLE 2 amide products 1 to 4 prepared

| Example | Amine/acid reagents | Mole |
|---|---|---|
| 1 | meta-Xylylenediamine | 0.46 |
|  | Hexamethylenediamine | 0.54 |
|  | 12-Hydroxystearic acid | 1.00 |
| 2 | meta-Xylylenediamine | 0.42 |
|  | Ethylenediamine | 0.18 |
|  | Hexamethylenediamine | 0.40 |
|  | 12-Hydroxystearic acid | 1.00 |
| 3 | 1,3-Bis(aminomethyl)cyclohexane | 0.46 |
|  | Hexamethylenediamine | 0.54 |
|  | 12-Hydroxystearic acid | 1.00 |
| 4 | 1,3-Bis(aminomethyl)cyclohexane | 0.42 |
|  | Ethylenediamine | 0.18 |
|  | Hexamethylenediamine | 0.40 |
|  | 12-Hydroxystearic acid | 1.00 |

IV—Evaluation of the Rheological Performance Qualities in a Paint Formulation

The amides prepared were evaluated in (reactive) epoxy paint formulations with a high solids content (or high dry extract) in xylene.

1) Preparation the Paint Formulations

A formulation known as "millbase" is prepared with the proportions presented in Table 3 below and in the following manner:

The following and successive operations are performed in a dispersing bowl (Dispermill® 2075 yellow line, supplier: Erichsen) heated via a jacket system:
1.1) Introduction of the epoxy binders and of the dispersant and the degassing agent. Homogenization is performed for 2 minutes at 800 revolutions/minute (800 rotations per minute or 800 rpm).
1.2) Introduction of the fillers and pigments, followed by milling at 3000 rpm for 30 minutes using a 7 cm paddle. The jacketed bowl allows this step to take place at room temperature with a bath of cold water (at 20° C.).
1.3) Introduction of the solvents (butanol according to Table 3) and homogenization.

2) Activation of the Amide Additive in the "Millbase"

24 hours after preparation of the millbase, the formulation is again dispersed using a 4 cm paddle at 3000 rpm. The diamide to be evaluated is introduced into the millbase and activated in situ at two tested activation temperatures, 50° C. and 70° C., for 20 minutes and at 3000 rpm.

The evaluation is not performed until 24 hours after the activation and 30 minutes after the addition into the millbase of the hardener diluted in xylene (see Table 4) and the paints thus obtained are adjusted as regards their paint application viscosity, with a xylene/butanol mixture (1/1 by weight) to about 0.4 P or about 40 mPa·s (more precisely to 0.37-0.38 P or 37-38 mPa·s) measured on cone 4 at 25° C. at 2500 s$^{-1}$ using a Brookfield® CAP 1000 viscometer. The proportions between the hardener and the solvent mixture are defined in Table 4 below. The amount of 1/1 xylene/butanol mixture used for the viscosity adjustment may vary, but in general by less than 1% (variation) from one test to another.

After the adjustment, the paint is mixed/homogenized at 1500 rpm for 2 minutes and then left to stand for 30 minutes before evaluation 24 hours later.

TABLE 3

"Millbase" formulation

| A-COMPOSITION of the Millbase | Function | Weight % |
|---|---|---|
| Araldite ® GZ 7071X75 | Binder | 17.3 |
| Araldite ® GY 783 BD | Binder | 12.9 |
| Byk ® A530 | Degassing agent | 0.5 |
| Disperbyk ® 110 | Dispersant | 0.5 |
| Tiona ® 595 (Titanium dioxide) | Pigment | 1.9 |
| Bayferrox ® 915 595 (iron oxide) | Pigment | 4.1 |
| ZP 10 (zinc phosphate) | Pigment | 7.5 |
| Finntalc ® MO5 | Filler | 9.4 |
| Silica HPF6 | Filler | 19.0 |
| n-Butanol | Solvent | 5.4 |
| Diamide 1, 2, 3 or 4 | Rheology additive | 0.8 |
| TOTAL |  | 79.3 |

TABLE 4 hardener

| B-Composition of the hardener | Mass % |
|---|---|
| Crayamid ® 140 | 8.8 |
| Xylene | 11.9 |
| TOTAL | 20.7 |

3) Evaluation of the Rheology of the Prepared Formulations of the Epoxy Paints and Results Various paint formulations were prepared with the prepared amides 1 to 4 according to the proportions shown in Tables 3 and 4 and with two activation temperatures examined, 50 and 70° C., according to the protocol outlined above.

The sag resistance and rheology results show that amide 3 based on 1,3-bis-(aminomethyl)cyclohexane has a thixotropic effect comparable or at least similar to that of amide 1 based on m-xylylenediamine for the same formulation activated at 50° C. or at 70° C.

The sag resistance and rheology results show that amide 4 based on 1,3-bis(aminomethyl)cyclohexane has a thixotropic effect comparable or at least similar to that of amide 2 based on m-xylylenediamine for the same formulation activated at 50° C. or at 70° C.

Consequently, amides 3 and 4 based on 1,3-bis(aminomethyl)cyclohexane have the necessary and very satisfactory characteristics of a rheology additive. The diamine 1,3-bis(aminomethyl)cyclohexane can therefore replace m-xylylenediamine in the context of the invention with results that are at least as good as those obtained without replacement, but, in the latter case, with the toxicity problem of said diamine not solved and drawbacks mentioned.

The sag resistance results are presented in Table 5 and the rheological performance results are presented in Table 6 below.

TABLE 5 sag resistance results

| Activation temperature (° C.) | Amide evaluated | Sag resistance (μm) |
| --- | --- | --- |
| 50 | 1 | 450 |
| 50 | 3 | 425 |
| 50 | 2 | 375 |
| 50 | 4 | 425 |
| 70 | 1 | 425 |
| 70 | 3 | 450 |
| 70 | 2 | 450 |
| 70 | 4 | 450 |

The rheological evaluation results (viscosity and thixotropic index TI 1/10 and TI 5/50) are presented in Table 6 below.

TABLE 6 rheological results

| Activation temperature (° C.) | Amide evalu-ated | Brookfield viscosity at 25° C. (mPa · s) at different rotation speeds of 1, 5, 10, 50 and 100 rpm | | | | | Thixotropic indices | |
| --- | --- | --- | --- | --- | --- | --- | --- | --- |
| | | 1 | 5 | 10 | 50 | 100 | TI 1/10 | TI 5/50 |
| 50 | 1 | 11600 | 3960 | 2640 | 1232 | 948 | 4.39 | 3.21 |
| 50 | 3 | 10200 | 3540 | 2360 | 1132 | 878 | 4.32 | 3.13 |
| 50 | 2 | 10200 | 3520 | 2380 | 1140 | 886 | 4.29 | 3.09 |
| 50 | 4 | 8800 | 3040 | 2060 | 1020 | 806 | 4.27 | 2.98 |
| 70 | 1 | 9600 | 3360 | 2260 | 1076 | 834 | 4.25 | 3.12 |
| 70 | 3 | 10400 | 3440 | 2280 | 1048 | 812 | 4.56 | 3.28 |
| 70 | 2 | 11800 | 3840 | 2540 | 1100 | 826 | 4.65 | 3.49 |
| 70 | 4 | 10000 | 3320 | 2200 | 1008 | 772 | 4.55 | 3.29 |

The invention claimed is:

1. Fatty acid diamide consisting of a product which is mixture of diamides, the product obtained from a reaction mixture comprising:
    a) at least one cycloaliphatic diamine comprising a ring of 6 carbon atoms,
    b) a fatty hydroxy acid chosen from the group consisting of 12-hydroxystearic acid (12-HSA), 9 hydroxystearic acid (9-HSA), 10-hydroxystearic acid (10-HSA), 14-hydroxyeicosanoic acid (14-HEA) and binary, ternary, and quaternary mixtures thereof,
    c) at least a second diamine selected from the group consisting of linear primary aliphatic C2 to C12 diamines,
    d) optionally, at least one monoacid selected from the group consisting of saturated and non-hydroxylated linear C6 to C18 carboxylic acids,
    e) optionally, at least a third primary diamine different from selected from the group consisting of linear aliphatic C2 to C12 diamines,
    f) at least one aromatic diamine chosen from the group consisting of xylylenediamines, said aromatic diamine optionally being partially or totally replaced with a cycloaliphatic diamine as defined in point a);
    said fatty acid diamine having a molar percentage of a/(a+f) of at least 50% and up to 100% and having a molar percentage of (a+f)/(a+c+e+f) from 30% to 80%.

2. The fatty acid diamide of claim 1, having a molar percentage of a/(a+f) of at least 50% up to 100%, and having a molar percentage of (a+f)/(a+c+e+f) from 30% to 65%.

3. The fatty acid diamide of claim 1 wherein said cycloaliphatic diamine a), is in the presence of xylylenediamines f), and in that said diamine a) represents from 50 mol % to 99 mol % of the total number of moles of diamines a)+xylylenediamine f).

4. The fatty acid diamide of claim 1 wherein said diamine f) is absent, with a mole ratio a/(a+f) of 100%, said cycloaliphatic diamine a) being 1,4-BAC or 1,3-BAC.

5. The fatty acid diamide of claim 1 comprising:
    i) a diamide consisting of the product of reaction of 1 mol of said diamine a) with 2 mol of said hydroxy acid b) as defined according to claim 1, and
    ii) a diamide consisting of the product of reaction of 1 mol of diamine c) with 2 mol of hydroxy acid b) as defined according to claim 1 and
    iii) a diamide consisting of the product of reaction of 1 mol of diamine according to e) and of 2 mol of hydroxy acid b) as defined according to claim 1.

6. The fatty acid diamide of claim 1 comprising at least 2 different reaction products as derived from the reaction between said diamines a), c) and e) and optionally the xylylenediamines f) and the monoacids b) and optionally d).

7. The fatty acid diamide of claim 1 wherein said monoacid d) is present in a proportion such that the mole ratio d/(b+d) is less than 0.5.

8. The fatty acid diamide of claim 1 in the form of a micronized powder having a mean size by volume of less than 20μ.

9. A method of gelling an organic solvent medium, said method comprising the step of adding the fatty acid diamide of claim 1 to the organic solvent medium.

10. Organogelling agent comprising at least one diamide of claim 1.

11. Organic binder composition comprising a rheology additive that is at least one diamide according to claim 1.

12. The organic binder composition of claim 11, wherein said binder is selected from the group consisting of: epoxy resins, unsaturated polyesters, vinyl esters, alkyds, silane resins, polyurethanes, polyester amides, solvent-based acrylic resins, acrylic monomers and oligomers, chlorinated elastomers, non-chlorinated elastomers, and chlorinated polymers other than chlorinated elastomers.

13. The fatty acid diamide of claim 1, wherein said cycloaliphatic diamine a) comprises, including said ring, from 6 to 18 carbon atoms, and is chosen from the group consisting of: 1,3-bis(aminomethyl)cyclohexane (1,3-BAC), 1,4-bis(aminomethyl)cyclohexane (1,4-BAC), 1,2-bis(aminomethyl)cyclohexane (1,2-BAC) and isomer mixtures thereof, decahydronaphthalenediamines, and isophoronediamines.

14. The fatty acid diamide of claim 1, wherein said cycloaliphatic diamine a) is chosen from the group consisting of 1,3-bis(aminomethyl)cyclohexane (1,3-BAC), and 1,4-bis(aminomethyl)cyclohexane (1,4-BAC).

15. The fatty acid diamide of claim 1, wherein said cycloaliphatic diamine a) is chosen from the group consisting of 1,3-bis(aminomethyl)cyclohexane (1,3-BAC), and 1,4-bis(aminomethyl)cyclohexane (1,4-BAC).

16. The fatty acid diamide of claim 1, wherein said cycloaliphatic diamine a) is 1,3-bis (aminomethyl) cyclohexane (1,3-BAC).

17. The fatty acid diamide of claim 1, wherein said hydroxy acid b) is chosen from the group consisting of 12-hydroxystearic acid, and a binary or ternary mixture of 12-hydroxystearic acid with hydroxy acid.

18. The fatty acid diamide of claim 1, wherein said aromatic diamine f) is m-xylylenediamine (m-XDA).

* * * * *